United States Patent [19]

Weinstock

[11] 4,053,286

[45] Oct. 11, 1977

[54] PROCESS FOR THE PREPARATION OF CEPHALOSPORIN ANTIBIOTICS

[75] Inventor: Leonard M. Weinstock, Belle Mead, N.J.

[73] Assignee: Merck & Co., Inc., Rahway, N.J.

[21] Appl. No.: 689,408

[22] Filed: May 24, 1976

Related U.S. Application Data

[63] Continuation-in-part of Ser. No. 507,473, Sept. 23, 1974, abandoned, which is a continuation-in-part of Ser. No. 420,418, Nov. 30, 1973, abandoned.

[51] Int. Cl.$^2$ ............................................. C07D 501/04
[52] U.S. Cl. ......................................... 544/21; 544/26; 424/246; 260/239.1
[58] Field of Search ................................... 260/243 C

[56] References Cited

U.S. PATENT DOCUMENTS

| | | | |
|---|---|---|---|
| 3,775,410 | 11/1973 | Christensen et al. | 260/243 C |
| 3,780,034 | 12/1973 | Christensen et al. | 260/243 C |
| 3,859,282 | 1/1975 | Cheng et al. | 260/243 C |

FOREIGN PATENT DOCUMENTS

| | | | |
|---|---|---|---|
| 2,096,117 | 1/1972 | France | 260/243 C |
| 1,348,986 | 3/1974 | United Kingdom | 260/243 C |

OTHER PUBLICATIONS

Karady et al., J. Am. Chem. Soc., 94 (4) 1410–1411 C(1972).

*Primary Examiner*—Nicholas S. Rizzo
*Attorney, Agent, or Firm*—Richard A. Thompson; Walter Patton; Julian S. Levitt

[57] ABSTRACT

An improved process for preparing the compound 7β-(2-thienylacetamido)-7-methoxy-3-carbamoyloxymethyl-3-cephem-4-carboxylic acid or its esters, from the compound 7β-(D-5-amino-5-carboxyvaleramido)-3-carbamoyloxymethyl-7-methoxy-3-cephem-4-carboxylic acid, by conducting the transacylation of the latter compound in the presence of commercially available alumino-silicate zeolites, also known as "molecular sieves." The process can be employed to prepare a cephalosporin with a desired 7-acylamido group from cephalosporins having a broad range of different 7-acylamido groups without having to isolate and purify a 7-amino intermediate. The final products have utility as broad spectrum antibiotics.

18 Claims, No Drawings

PROCESS FOR THE PREPARATION OF CEPHALOSPORIN ANTIBIOTICS

RELATIONSHIP TO PRIOR APPLICATIONS

This application is a continuation-in-part application of my co-pending application, U.S. Ser. 507,473, filed Sept. 23, 1974, now abandoned, which is a continuation-in-part application of my co-pending application, U.S. Ser. 420,418, filed Nov. 30, 1973, now abandoned. This invention is an improvement over the acylation process for preparing 7-acylamido cephalosporins as disclosed and claimed in co-pending U.S. Ser. 149,364, filed June 2, 1971.

BACKGROUND OF THE INVENTION

One method of producing 7-acylamido cephalosporins, used medicinally as antibiotics, comprises preparing the analogous 7-amino cephalosporin and then acylating the 7-amino group to produce the desired product. This method suffers from the disadvantage that it is necessary to first isolate and purify the intermediate 7-amino cephalosporin. Accordingly, other methods have been sought which would avoid the need of preparing the 7-amino cephalosporin intermediate.

More recently it has been found that 7β-acylamido cephalosporins having a methoxy substituent in place of the hydrogen substituent at the 7-position are produced by various microorganisms. These cephalosporins contain an aminoadipoyl sidechain at the 7-position which is preferably interchanged with an acyl sidechain which provides a 7β-acylamido-7α-methoxy cephalosporin of enhanced antibiotic activity.

SUMMARY OF THE INVENTION

In accordance with the present invention, we have found that the acyl group, B', of 7-acylamido cephalosporin compounds can be interchanged by another acyl group, R', as follows:

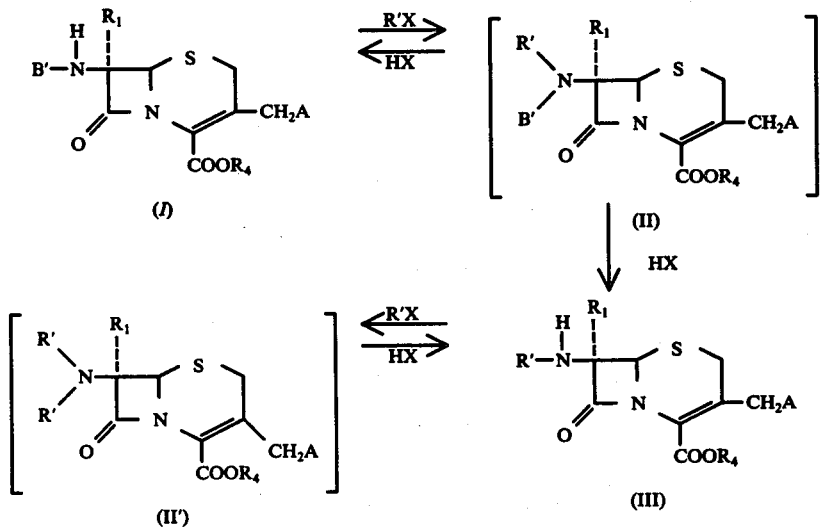

in which B' and R' represent different acyl groups, $R_1$ represents hydrogen or a substituent such as methoxy, and $R_4$ represents hydrogen or an easily removable blocking group and A is hydrogen or other substituent known in the art.

Both B' and R' can be represented by the general formula

wherein $R_6$ and $R_7$ are as defined below, and represent a preferred group of substituents because of their generally useful antibiotic activity. $R_6$ represents hydrogen, halo, amino, guanidino, phosphono, hydroxy, tetrazolyl, carboxy, sulfo or sulfamino. $R_7$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino, guanidinomethyl, carboxamethyl, aminomethyl, nitro, methoxy or methyl. Examples of the preferred acyl groups, either B' or R', that might be mentioned are phenylacetyl, 3-bromophenylacetyl, p-aminomethylphenylacetyl, 4-carboxylmethyl-phenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl; 3-methyl-1,2,5-oxadiazolylacetyl; 1,2,5-thiadiazolyl-4-acetyl; 3-methyl-1,2,5-thiadiazolyl-4-acetyl; 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl. It is generally necessary to protect reactive groups, such as amino, hydroxy and guanidino groups present in the acylating agents during the transacylation and removing said protecting groups when the transacylation is completed. This is done by methods well known to those skilled in the art.

$R_4$ represents the radical of an alcohol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-methylthioethyl, 2-(p-methylphenyl)ethyl, 2-(p-methylphenyl)sulfonylethyl, 2-(methylaminoethyl, 2-chloro-(or bromo)ethyl, benzyl, a substituted benzyl group such as p-nitrobenzyl, p-methoxybenzyl, 3,5-dinitrobenzyl, 2,4,6-trimethylbenzyl, 3,5-dichloro-4-hydroxybenzyl, and the like, a benzhydryl or substituted benzhydryl group such as p-methoxybenzhydryl, an acyloxy alkyl group such as acetoxymethyl, pivaoloyloxymethyl, an alkoxy group such as methoxymethyl, or a monocyclic aryl group for example phenyl or substituted phenyl such as p-nitrophenyl or 3,5-dinitrophenyl or an acyl group such as acetyl, benzoyl or thienylacetyl. It has been found that the most convenient group used for the purpose of blocking the carboxy group is the methoxymethyl group. These protecting or blocking groups for the carboxy substituents are readily prepared in accordance with process well known in this art.

A is hydrogen or other substituents known in the art. The substituent A can represent azido, halo, cyano, alkoxy, aryloxy, aralkyloxy, heterocycleoxy, blocked mercapto, alkylthio, arylthio, aralkylthio, heterocyclethio, blocked amino, blocked hydroxy, alkylamino, alkanoylamino, blocked hydroxyphenyl, acylthio, acyloxy, sulfamoyloxy, and the like. The heterocycles can be a 5- or 6-membered hetero ring containing one or more nitrogen, oxygen or sulfur atoms, such as (1-methyl-1,-2,3,4-tetrazolyl). The acyl group can be a loweralkanoyl group of 2-6 carbon atoms, or thiocarbamoyloxy and N-alkyl or N, N-dialkyl derivatives of carbamoyloxy or thiocarbamoyloxy. The alkyl group of the foregoing substituents contains 1-6 carbon atoms and may be further substituted radicals such as alkoxy, halo, blocked amino, cyano, carboxy, sulfo and the like. The blocking groups referred to are easily removable blocking groups well known in the art. The substituent A includes the lactone formed by a hydroxymethyl group at the 3-position and the carboxylic acid group at the 4-position; the substituent A also includes the lactam formed by an aminomethyl group at the 3-position and the carboxylic acid group at the 4-position.

The acylating agent, R'X, can be an acyl halide, an anhydride, or a mixed anhydride although generally it is preferred to use an acyl halide, for example an acyl chloride, as the acylating agent.

Thus, in the above flowsheet the cephalosporin compound (I) is reacted with an acylating agent, R'X, in the presence of a molecular sieve catalyst to produce the 7-diacylimido cephalosporin compound (II) which is then cleaved to remove the acyl group, B', to produce the new 7-acylamido cephalosporin compound (III). The net result is the interchange of the acyl group, B', for the acyl group, R'. This process is hereinafter referred to as transacylation.

The step of producing the diacylimido product is best effected by intimately contacting the cephalosporin compound with an acylating agent in a suitable solvent medium in the presence of molecular sieves. The temperature at which the reaction is carried out is not particularly critical and temperatures from about 0° C. to about 120° C. are generally satisfactory, although it is preferred to carry out the reaction at temperatures from about 50° C. to 90° C. Solvents which do not contain an active hydrogen such as chloroform, acetonitrile, methylene chloride, ethylene dichloride, dioxane, benzene, halobenzene, carbon tetrachloride, diethylether, and the like are suitable mediums for carrying out this reaction. When the reaction carried out at a temperature above the boiling point of the selected solvent, the reaction is carried out in an autoclave using methods known to those skilled in the art.

The molecular sieves which are useful in this invention are alumino-silicate zeolites. Generally speaking, naturally-occurring zeolites can be defined as a group of crystalline solids, hydrated alumino-silicates of mono- and divalent bases, which are capable of losing part or all of their water without change of crystal structure, adsorbing other compounds in place of the water removed, and which are capable of undergoing base exchange. A synthetic zeolite, on the other hand, is synthesized from a combination of basic oxides ($AlO_2$, $SiO_2$, $Na_2O$, $K_2O$, etc.) in an aqueous system to yield a hydrated or semi-hydrated crystalline structure. Following heat treatment, the zeolites can be considered substantially anhydrous. Synthetic zeolites are characterized and classified primarily by X-ray powder diffraction methods. Although there is lack of a systematic chemical method for naming synthetic, complex alumino-silicates, historically each new synthetic zeolite is assigned an arbitrary letter or group of letters and numbers. The meaning of these arbitrary symbols is well understood by those skilled in the art.

It has been found that synthetic zeolites of the A and X classes are particularly advantageous to employ in the transacylation process described above. The pore size of the zeolites can be in the range of from about 3 to about 15 A. The zeolites can be substantially anhydrous or contain some water of hydration. The amount of water by weight contained in the zeolite can be from 0-30%.

When the transacylation process of the present invention is carried out using molecular sieves containing less than 10% by weight water the process is hereinafter referred to as the "dry sieve" transacylation process. When the transacylation process is carried out using molecular sieves containing more than 10% by weight water, the process is hereinafter referred to as the "wet sieve" transacylation process. The significance of the "dry" and "wet" process will be made clear hereinafter.

The reaction (I)⇌(II) schematically represented above is an equilibrium reaction. The reaction of (I) with an acylating agent, R'-halide, which represents the reaction in the forward direction (I)→(II) results in the formation of diacylimido intermediate compound (II) and an equivalent amount of hydrohalic acid. The acylating agent, R'-halide, is preferably present in an excess amount, preferably in the range of 1 to 4 molar excess or most preferably in the range of 3 to 4 molar excess. However, this is not essential and desired product, (III), may be obtained with an equimolar amount of acylating agent, R'-halide.

The reaction of (II) with hydrohalic acid, represents the reverse of the reaction (I)→(II). The reverse of the reaction (I)→(II) results in the cleavage of an acyl group. In the compound (II) either of the acyl groups R' or B' may be cleaved. Cleavage of R' results in the formation of the starting material with no net change. Cleavage of B' results in the formation of the desired product (III). The presence of an excess of R'-halide favors the formation of high yields of the product (III).

The final product (III) is in equilibrium with the diacylimido compound (II') wherein both acyl groups are R'. The desired product, (III), is obtained from (II')

by the cleavage of one of the two R' groups with hydrohalic acid.

The cleavage of the acyl groups in the equilibrium reactions above is accomplished by hydrohalic acid. The hydrohalic acid is formed from a number of sources. Firstly, the reaction of the compound (I) with an acyl halide results in formation of an equivalent amount of hydrohalic acid is situ. Accordingly, merely by prolonging the reaction time, the hydrohalic acid formed in situ provides the desired product (III). Secondly, in the case wherein the "wet sieve" method is used (sieves contain more than 10% water by weight) the water hydrolyzes excess acid acylating agent to provide hydrohalic acid. Both of these methods can be characterized as "passive" in the sense that there is no need to add a separate "cleaving agent" to the reaction mixture.

A third method of providing a hydrohalic acid for cleaving the diacylimido intermediate to the final product (III) is by the addition to the reaction mixture of a compound which on contact with excess acyl halide, hydrolyzes the acyl halide to provide a hydrohalic acid. Alcohols such as benzyl alcohol, alkanols of 1 to 6 carbon atoms or lower alkyl thiols of 1 to 6 carbon atoms are useful for this purpose. This method of generating hydrohalic acid is preferred when the transacylation is carried out by the "dry sieve" method wherein the sieves contain less than 10% water by weight. Finally, a hydrohalic acid such as hydrochloric acid can be added to the reaction mixture as a cleaving agent.

DESCRIPTION OF THE PREFERRED EMBODIMENTS

In accordance with a preferred embodiment of the present invention, it is now found that 7β-aminoadipoyl cephalosporins such as those obtained by fermentation of various *Streptomyces* species such as *S. clavuligerus, S. lipmanii* or *S. lactamdurans,* can be converted to derivatives having a different acyl group in place of the aminoadipoyl group without first cleaving this group and then reacylating the intermediate 7-amino compound. The general process is illustrated in the following flowsheet:

In the formulas of the above flowsheet, $R_1$ represents hydrogen or methoxy; A is as defined above, most desirably, acetoxy or carbamoyloxy; R' represents an acyl group as defined above; $R_4$ represents hydrogen or a blocking or protecting substituent; and $R_2$ represents hydrogen or an amino blocking or protecting substituent.

The side chain carboxyl protecting group, $R_4$, and side chain amino protecting group, $R_2$, in compound (V) do not have to be easily removable since the side chain is removed in the transacylation process. It is preferred that the side chain amino protecting group be one that is not easily removed since these are usually less expensive and more stable to handling during manufacturing. However, the $R_4$ group at the 4-carboxyl group should be easily removed using methods available in the art.

In accordance with the above flowsheet, the cephalosporin compound (IV) or a derivative thereof wherein the amino substituent and/or the carboxy groups are optionally blocked or protected (V) is reacted with an acylating agent in the presence of the molecular sieve to produce the intermediate diacylimido product (VI). The aminoadipoyl moiety of the latter product is then cleaved to produce the new acylated cephalosporin compound (VII), or a salt thereof when $R_4$ is hydrogen.

Although this invention can be carried out without blocking or protecting the amino and carboxy groups of the starting cephalosporin compound (IV), it is generally preferred to carry it out by first blocking or protecting both the amino and carboxy groups since maximum yields of the desired new cephalosporin compound are obtained with such protected compounds. It is generally necessary to protect reactive groups, such as amino, hydroxy and guanidino groups present in the acylating agents during the transacylation and removing said protecting groups when the transacylation is completed. This is done by methods well known to those skilled in the art.

An illustrative, more detailed description of this preferred process of our invention is shown in the following flowsheet:

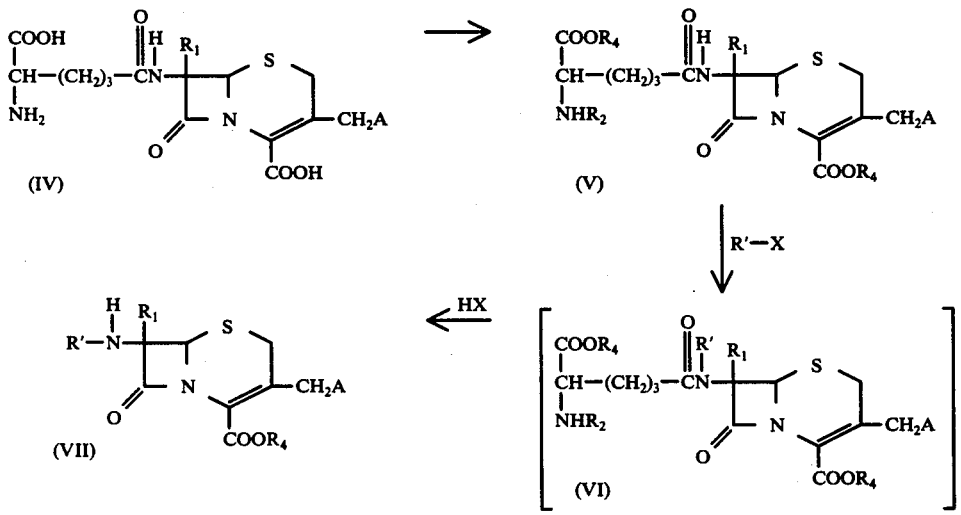

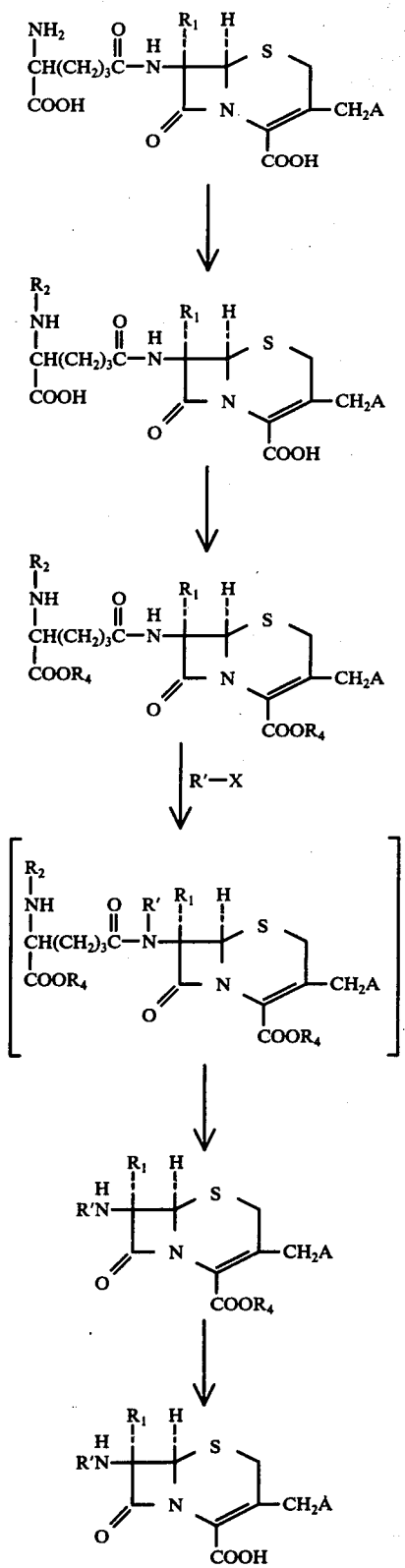

wherein $R_1$ represents hydrogen or methoxy, A is carbamoyloxy or acetoxy, and $R_2$ represents an amino blocking group. The moiety $COOR_4$ indicates a blocked carboxy group wherein $R_4$ is a blocking group and R' represents an acyl group as defined above.

In accordance with this process, the amino group of the starting cephalosporin compound (VIII) is first blocked ($R_2$) by reaction with a suitable reagent to protect the 5'-amino-substituent of the aminoadipoyl side chain. Thus, the amino group is blocked by amino protecting groups such as acyl, aroyl, alkoxycarbonyl, alkylsulfonyl, arylsulfonyl, and the like in accordance with methods well known in this art. Specific groups suitable for blocking the amino group that might be mentioned are those wherein $R_2$ is trichloroethoxycarbonyl, teritary butoxycarbonyl, benzoylmethoxycarbonyl, trimethylsilyl, p-methoxybenzyloxy, 2-nitrophenylsulfenyl, 2,4-dinitrophenylsulfenyl, chloroacetyl, p-nitrophenylthio, p-nitrobenzenesulfonyl, p-toluenesulfonyl, methanesulfonyl, benzoyl, p-chlorobenzoyl, p-nitrobenzoyl, toluoyl, and the like, although we generally prefer to utilize the p-toluenesulfonyl or benzoyl derivative which is conveniently prepared by reacting the cephalosporin compound with p-toluenesulfonyl chloride or benzoyl chloride while keeping the pH of the mixture basic, i.e., between 9 and 10.

In is generally preferred to carry out the above-described reactions with a cephalosporin compound, (X), wherein the carboxy groups on the aminoadipoyl side chain, and at the 4-position are likewise blocked or protected since maximum yields of the desired product are obtained with such derivatives. Although the carboxy group on the aminoadipoyl side chain is not necessarily deblocked, since it is removed in the cleavage step, the blocking or protecting group at the 4-position is preferably one which can be removed easily to obtain the free acid without disruption of the β-lactam group since the cephalosporin compounds are usually used in the form of salts such as alkali metal salts or an amine salt. Protecting groups suitable for this purpose are well known in this art.

The protected cephalosporin compound is then reacted with an acylating agent, R'X, in the presence of the molecular sieve such as those described above to obtain the diacylimide product (XI). The acylating agent can be an acid halide (chloride or bromide), or a functional equivalent thereof such as an acid anhydride, a mercaptide, a mixed acid anhydride with other carboxylic acids, an activated ester of the carboxylic acid such as the p-nitrophenyl ester, and the like. The acid chloride is preferred.

The preferred acylating agents used in the process of the present invention are those of carboxylic acids. The preferred acyl groups representing R' in the above flowsheet are those of the general formula:

$$R_3-\underset{\underset{Y}{|}}{CH}-\overset{\overset{O}{\|}}{C}$$

wherein Y is hydrogen, halogen, protected amino, azido, protected guanidino, phosphono, hydroxy, protected hydroxy, tetrazolyl, carboxy, protected carboxy, sulfo, or sulfamino; $R_3$ is phenyl, substituted phenyl, a monocyclic heterocyclic 5- or 6-membered ring containing one or more oxygen, sulfur or nitrogen atoms in the ring, substituted heterocycles phenylthio, phenyloxy, heterocyclic or substituted heterocyclic thio groups, loweralkyl (1-6 carbon atoms), or cyano; the substituents on the $R_3$ group being halo, carboxymethyl, guanidino, guanidinomethyl, carboxamidomethyl, aminomethyl, nitro, methoxy or methyl.

Further preferred acyl groups representing R' in the above flowsheet are those of the general formula:

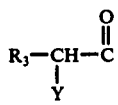

wherein Y is hydrogen, carboxy; $NHR_2$ or $-OR_5$; $R_2$ is hydrogen, trichloroethoxycarbonyl, tertiary butoxycarbonyl, benzoylmethoxycarbonyl, p-methoxybenzyloxy, 2-nitrophenyl-sulfenyl, 2,4-dinitrophenylsulfenyl, chloroacetyl, p-nitrophenylthio, p-nitrobenzenesulfonyl, p-toluenesulfonyl, methanesulfonyl, benzoyl, p-chlorobenzyl, p-nitrobenzoyl or toluoyl; when $R_2$ is hydrogen the acylating agent is employed as the hydrohalide salt such as a hydrochloride.

$R_5$ is hydrogen or a hydroxy protecting group. The protecting groups, $R_5$, used for protecting the OH group of an alcohol are similar to those for protecting the OH of a carboxylic acid. The hydroxy protecting groups are well known to those skilled in the art and include ethers, mixed acetals, acyl groups and silyl groups. The preferred hydroxxy protecting groups are where $R_5$ is methyl, ethyl, phenacyl, p-bromophenacyl, 2,2,2-trichloroethyl, benzyl, p-nitrobenzyl, p-methoxybenzyl, 3,5-dinitrobenzyl, 2,4,6-trimethylbenzyl, benzhydryl, p-methoxybenzhydryl or methoxy-methyl; and $R_3$ is phenyl, 2-thienyl, 3-thienyl, 2-furyl, 3-furyl, 1-tetrazoyl, $C_1$ to $C_4$ loweralkylphenyl, halophenyl, protected hydroxyphehyl or a $C_1$ or $C_4$ loweralkyloxyphenyl.

When the acylating agent contains groups such as amino, hydroxy or carboxy, these groups can be blocked or protected during the acylation reaction and later removed in accordance with methods known in the art. Suitable blocking agents for the amino group are defined above as $R_2$. Suitable blocking groups for carboxy are defined above as $R_4$ and for hydroxy as $R_5$. Alternatively, the acylating agent can contain a substituent such as azido which can be later reduced to an amino substituent pursuant to known methods.

Especially preferred acylating agents that might be mentioned are those having an acetyl or substituted acetyl group such as phenylacetyl, thienylacetyl (2- and 3-thienylacetyl), furylacetyl, (2- and 3-furylacetyl), α-hydroxyphenylacetyl, phenoxyacetyl, α-formyloxyphenylacetyl, 1-tetrazolylacetyl, α-aminophenylacetyl, hydrochloride, phenylthioacetyl, α-azidophenylacetyl, and others as the resulting acylated cephalosporin compounds have enhanced antibiotic activity.

The acylating agent is employed in amounts in molecular excess of that of the starting cephalosporin, preferably from 1 to 6 times as much acylating agent as cephalosporin, preferably in the range 1 to 4 molar excess or most preferably in the range of 2 to 4 molar excess.

The molecular sieve used is any of a number readily and commercially available. Preferably, a synthetic zeolite of regular crystal structure and uniform pore size is used. The most commonly available sieve, Type 3A, 4A, 5A, and 13X, are all operable in the invention. These sieves have the following properties:

| Type | Formula | Pore Diameter |
|---|---|---|
| 3A | $K_xNa_{12-x}[(AlO_2)_{12}(SiO_2)] \cdot 27H_2O$ | 3A |
| 4A | $Na_{12}[(AlO_2)_{12}(SiO_2)] \cdot 27H_2O$ | 4A |
| 5A | $Ca_{4.5}Na_3[(AlO_2)_{12}] \cdot 30H_2O$ | 5A |
| 13X | $Na_{86}[(AlO_2)_{86}(SiO_2) \cdot 106-xH_2O$ | 10A |

The sieves are available in substantially anhydrous form; they can be used in this form or dehydrated further, to 0% water ± 2% water, by heating to high temperatures (about 500° C. or above) before use in the "dry sieve" method; or can be used when they contain up to about 30% water of hydration (weight % basis) for the "wet sieve" method. The hydrated sieves are prepared by allowing them to stand in a high humidity chamber or environment or by slurrying in water and then adjusting to desired moisture content by vacuum drying or drying at room temperature or at elevated temperature.

Generally, this drying takes about 2-5 hours, although it is not a critical time limit. Moisture level can be measured using the Karl Fischer method, a generally accepted technique, or by other available methodology.

The steps of converting the protected cephalosporin compound (X) to the diacylated imide product (XI) is preferably effected by intimately contacting the cephalosporin compound with the acylating agent in a suitable solvent medium in the presence of the desired molecular sieve. The temperature at which this reaction is carried out is not critical, and temperatures from about −0° C. to about 100° C. are generally satisfactory. However, since the reaction appears to be temperature dependent, and proceeds faster at higher temperatures, it is preferred to carry out the reaction at temperatures from about 50° C. to 90° C. Various solvents which do not contain an active hydrogen such as chloroform, acetonitrile, methylene chloride, dioxane, benzene, halobenzene, carbon tetrachloride, 1,2-dichloroethane, and diethylether are most suitable as mediums for the reaction mixture. It is important to keep the slurry in motion by stirring or agitating during the reaction.

The amount of sieves necessary for the transacylation reaction can be varied to suit the chosen operating conditions. Generally, it is preferred to use approximately equal amounts of weight of the starting material and the sieves, although it is possible to use a weight ratio of starting compound to sieves of 1 to 0.5-2.

As mentioned above, the original acyl group is cleaved by a number of different routes. Simple "aging" of the reaction mixture is enough in some cases, e.g., when the sieves contain between 10-30% water, for from 30 minutes to 30 hours. An alkanol, loweralkyl thiol, or benzyl alcohol can be added following a briefer "aging" period. The alkanol or loweralkyl thiol can have 1-6 carbon atoms, and preferably is methanol, ethanol, isopropanol, or t-butanol. Hydrochloric acid can also be added to effect cleavage. During the acylating reaction some "spontaneous" cleavage of the aminoadipoyl group occurs, due to the equilibrium nature of the reaction, depending upon the conditions under which the acylation is effected. Prolonged heating of reaction mixture results in the cleavage of the aminoadipoyl group and the preparation of the desired 7-acylated cephalosporin compound, especially when the sieves contain less than about 10% water.

The removal of the protective or blocking group on the 4-carboxy function is accomplished in accordance with procedures well known in the art. Thus, for example, the methoxymethyl group is removed by the use of hydrochloric acid at 0°-10° C.; the trichloroethoxycarbonyl group is removed by reaction with zinc and acetic acid; and the t-butoxycarbonyl and benzhydryl groups are removed by reaction with trifluoroacetic acid. Other removals are accomplished with similar ease.

EXAMPLE 1

3-Carbamoyloxymethyl-7-methoxy-7β-thienylacetamido-3-cephem-4-carboxylic Acid

Step a; 7β-(D-5-tosylamino-5-carboxyvaleramido)-3-carbamoyloxymethyl-7-methoxy-3-cephem-4-carboxylic Acid The mono-sodium salt of 7β-(D-5-amino-5carboxyvaleramido)-3-carbamoyloxymethyl-7-methoxy-3-cephem-4-carboxylic acid (45.0 ml. of 49.5 mg./ml. aqueous solution) mixed with acetone (450 ml.) and water (450 ml.). The pH of the mixture is adjusted to 9.5–9.6 with 50% NaOH solution and tosyl chloride (19 g.) in acetone (100 ml.) is added in portion. The pH is maintained at 9.5–9.6 by frequent addition of caustic solution. After 15–20 minutes the pH becomes stable; sulfonylation continues for a total of 1 hour. The temperatures of the solution is 20°–23° C., throughout the entire reaction period.

After this, the solution is cooled in an ice bath and the pH is lowered to 7 by the addition of 1:1 HCl (ice cold). The solution is extracted using ethyl acetate. The ethyl acetate layer is backwashed with 100 ml. 5% sodium chloride solution. The organic layer is discarded and the aqueous layers together with 500 ml. of ethyl acetate are readjusted to 2.5 and the layers are separated. The aqueous layer is extracted further with 3 × 500 ml. EtOAc. The ethyl acetate layer is backwashed with 100 ml. sat. NaCl solution. The ethyl acetate extracts are dried with $Na_2SO_4$ and the solvent is concentrated to a small volume. (Temperature 30° C.).

The concentrated solution is then dissolved in 200 ml. of isopropanol, heated to 40°–45° C., and 5.8 ml. acetic acid, and 21.6 ml. of dicyclohexylamine added.

This slurry is allowed to cool slowly and is aged overnight at room temperature. The product is filtered, washed with 100 ml. of isopropanol and dried overnight at room temperature under high vacuum.

The product, 7β-(D-5-tosylamino-5carboxyvaleramido)-3-carbamoyloxymethyl-7-methoxy-3-cephem-4-carboxylic acid, dicyclohexylamine salt, is obtained in a yield of 44.5 g.;

uv: (pH 7.0 buffer)
λmax. 2620 A E% 94.7
Equivalent wt. ($HClO_4$ titration) 481.5 (theory 481.5)
Anal. calculated for $C_{47}H_{74}N_6O_{11}S_2$: C, 58.60; H, 7.74; N, 8.72; Found: C, 58.29; H, 7.29; N, 8.73.

Step b: Dimethoxymethyl ester of 7β-(D-5-tosylamino-5-carboxy valeramido)-3-carbamoyloxymethyl-7-methoxy-3-cephem-4-carboxylic acid The tosyl salt from Step a, 20 g., is charged to a 3-necked flask. Methylene chloride (200 ml.) is added and the slurry is cooled to 0° C. in an ice bath, under nitrogen. Chloromethyl methylether (4.1 ml.) in 30 ml. of methylene chloride is added to the reaction mixture over a period of 90 minutes, with good agitation and ice cooling. After 1 hour addition time, a solution of collidine (1.58 ml.) in 5 ml. of methylene chloride is introduced.

After additions, the mixture is agitated for an additional 2 hours, filtered, and the filter cake washed with dry methylene chloride. After extraction with aqueous phosphoric acid, sodium chloride, sodium bicarbonate, and sodium chloride solutions, the filter cake is back washed with methylene chloride. The organic layer is dried, filtered, concentrated to a small volume, and crystallized. The product, the dimethoxymethyl ester of 7β-(D-5-tosylamino-5-carboxyvaleramido)-3-carbamoyloxymethyl-7-methoxy-3-cephem-4-carboxylic acid, is obtained as 9.6 g. (yield 83.5%). Both ultraviolet and thin layer chromatography indicated only the single component in the product.

Step c: 3-Carbamoyloxymethyl-7-methoxy-7β-thienylacetamido-3-cephem-4-carboxylic acid To a stirred slurry of 6.9 g. of tosyl methoxymethyl ester from Step b and 7.5 g. of type 4A powdered molecular sieves (600 mesh, hydrated to 17% ± 2% water) in 85 ml. of 1,2-dichloroethane was added 5 ml. of distilled 2-thienylacetyl chloride. The stirred slurry was heated at 65° C. for 16 hours under a nitrogen atmosphere.

The reaction is monitored using thin layer chromatography. After the time indicated, the major component of the reaction mixture is the desired intermediate compound. Methanol (0.8 ml.) is then added, and the slurry aged an additional 2 hours. At this point, the 4-methoxymethyl ester of the desired product is the predominant compound in the slurry.

The ester is hydrolyzed by cooling the solution above to 25° C., filtering, and washing with cold methanol. The filtrate and wash are combined and cooled to 0° C. A 0° C. solution of 20.8 ml. conc. HCl and 23.6 ml. methanol are added and the solution warmed to 15° C. and stirred at 15° C. for 2 hours, 40 minutes. A thin layer chromatographic analysis is run at this point. The pH of the mixture is adjusted by first bubbling in ethylene oxide as necessary to adjust the pH to between 2–2.5; then bringing up the pH to between 5–6 by addition of solid sodium hydroxide. The mixture is filtered, and the dichloroethane layer is separated. The cold aqueous layer contains the sodium salt of the product. This layer is purified using column chromatography, using IRA-68 resin on the nitrate cycle, the eluant being 0.02M phosphate buffer pH 7.0. The final yield of product is 1.74 g., showing a single spot on thin layer chromatography. The angle of rotation is 192°. Product identity is confirmed by NMR; the product is the desired 3-carbamoyloxymethyl-7-methoxy-7β-thienylacetamido-3cephem-4-carboxylic acid, m.p. 165°–167° C.

The starting material, the monosodium salt of b 7β-(D-5-amino-5-carboxyvaleramido)-3-carbamoyloxymethyl-7-methoxy-3-cephem-4-carboxylic acid, used in the foregoing example is prepared as follows:

Preparation of Monosodium Salt of 7β-(D-5-amino-5-carboxyvaleramido)-3-carbamoyloxymethyl-7-methoxy-3-cephem-4-carboxylic Acid Modified Fermentation Process Step 1: Slants A lyophilized tube of *Streptomyces lactamdurans* culture (NRRL 3802) was opened aseptically and the organism transferred to a medium of the following composition:

Medium XI
1% Blackstrap Molasses
1% National Brewer's Yeast
2.5% Difco agar pH 7.0
Water to volume The slants are incubated for 7 days at 28° C. When stored in the cold, the slants are stable for more than 13 weeks.

Step 2: Seed Stages: Two Stage System

First Seed

The first seed is inoculated directly from the slant of Step 1 to 40 ml. of 1% Primary Dried Yeast N.F., pH 7.0 (obtained from the Yeast Product Corporation) in a 250 ml. baffled Erlenmeyer flask. The flasks were then shaken on a 220 rpm rotary shaker with a 2 inch throw at 28° C. for a period of from 2 to 3 days.

Second Seed

A 2.5% inoculum from the first seed stage was added to a flask containing a 2% Fleischmann S-150 yeast autolysate, pH 7.0. The growth in this stage is characteristically light and the incubation, performed as in the first stage, was not extended beyond 48 hours.

Step 3: Production Medium

The production medium contains per liter of distilled water 30 g. distiller's solubles, 7.5 g. of Primary Dried Yeast N.F. and 0.25% v/v of an emulsified petroleum product (Mobilpar-S)defoamer. The medium is adjusted to pH 7.0 with a small amount of concentrated sodium hydroxide solution dispensed into Erlenmeyer flasks and autoclaved for 15 to 20 minutes at 121° C. After cooling the medium received a 2.5% inoculum of the seed obtained in Step 2. The time of incubation can vary from about 50 to 100 hours but an incubation period of about 72 hours is preferred. The volume of media in each flask can vary from 30 to 50 ml. but 40 ml. was used routinely. The level of inoculum can vary from 1 to 5%; but, in practice, a 2.5% level is generally employed.

Step 4: Assay

When the fermentation was complete, the cells were removed by centrifugation and the broth was diluted with phosphate buffer, pH 7.0. The concentration of 7β-(D-5-amino-5-carboxyvaleramido)-3-carbamoyloxymethyl-7-methoxy-3-cephem-4-carboxylic acid in the fermentation broth was determined by the standard biological-disc assay method. The assay organism employed was *Vibrio percolans* (ATCC 8461). Filter paper discs are immersed into the diluted broths and placed on the surface of agar-containing Petri dishes which were inoculated with the assay organism *Vibrio percolans* (ATCC 8461). Also placed on these Petri dishes are discs that had been dipped previously in standard solutions containing known concentrations of 7β-(D-5-carboxyvaleramido)-3-carbamoyloxymethyl-7-methoxy-3-cephem-4-carboxylic acid. The discs were incubated overnight at 28° C. and the diameters of the zones of inhibition recorded. The concentration of product and the fermented broth is calculated by interpolation from the standard curve which relates zone diameter with the known concentrations of standard solutions of the product. By this procedure, it was calculated that *Streptomyces lactamdurans* NRRL 3802 produced 78.6 µg./ml. of 7β-(D-5-amino-5-carboxyvaleramido)-3-carbamoyloxymethyl-7-methoxy-3-cephem-4carboxylic acid in the modified fermentation process.

Step 5: Isolation

The filtered broth is adjusted to pH 7.0 with dilute hydrochloric acid and 2900 ml. is passed through a column containing a strongly basic anion exchange resin (100 g.) having a styrene-divinylbenzene matrix (Dowex 1 × 2 chloride cycle resin) at 10 ml./minute. The spent is collected in 500 ml. fractions. The resin column is washed with water and eluted with 3% ammonium chloride in 90% methanol. The eluate is collected in 100 ml. fractions. The activity of the fraction is monitored; the most active fractions are combined, the pH adjusted to pH 7.2 to 8.0 with dilute sodium hydroxide and adsorbed on a strongly basic anion exchange resin ( 100 g.) having a styrene-divinylbenzene matrix (Dowex 1 × 2 chloride cycle resin) at 14 ml./minute. The column is washed with water and eluted with 5% aqueous sodium chloride. The concentrate is diluted to 500 ml., adjusted from pH 8.8 to pH 2.0 with dilute hydrochloric acid and adsorbed on 25 ml. of a strongly acidic cation exchange resin of the sulfonate type having a styrene-divinylbenzene matrix (Dowex 50 × 2 hydrogen cycle resin) at 2.5 ml./minute. The column is washed with 25 ml. of water then eluted with 2% pyridine until the pH of the column effluent rose to pH 7.0 (54 ml.). The eluate thus obtained is adjusted to pH 8.0 with dilute sodium hydroxide and concentrated under vacuum to remove the pyridine and afford the monosodium salt of 7β-(D-5-amino-5-carboxyvaleramido)-3-carbamoyloxymethyl-7-methoxy-3-cephem-4-carboxylic acid.

Elemental analysis for $C_{16}H_{21}N_4SO_9Na$: Calculated: C, 41.0%; H, 4.5%; N, 12.0%; S, 6.8%. Found: C, 39.31%; H, 4.76; N, 11.16%; S, 6.46%.

EXAMPLE 2

3-Carbamoyloxymethyl-7-methoxy-7β-phenylacetamido-3-cephem-4-carboxylic acid

Step A; Dimethoxymethyl ester of 7β-[(D-5-tosylamino-5-carboxyvaleryl)-phenylacetylamido]-3-carbamoyloxymethyl-7-methoxy-3-cephem-4-carboxylic Acid A solution of the dimethoxymethyl ester of 7β-(D-5-tosylamino-5-carboxyvaleramido)-3-carbamoyloxymethyl-7-methoxy-3-cephem-4-carboxylic acid (9.3 gm., 10 mmoles), type 12A powdered molecular sieves (hydrated to 20% ± 2% water) (10.8 gm.), and phenylacetyl chloride (5.3 ml., 40 mmoles) in 50 ml. of acetonitrile is heated to 40° C. for 20 hours. After this period the mixture is cooled to room temperature and filtered. The filtrate is evaporated to dryness and triturated with hexane. The insoluble residue containing dimethoxymethyl ester of 7β-[(D-5-tosylamino-5-carboxyvaleryl)phenylacetylamino]-3-carbamoyloxymethyl-7-methoxy-3-cephem-4-carboxylic acid, is used without purification in the next step.

Step B: 3-Carbamoyloxymethyl-7-methoxy-7β-phenylacetamido-3-cephem-4-carboxylic Acid The crude product from Step A is dissolved in 50 ml. 1,2-dichloroethane. 1.0 Ml. of methanol is then added and the solution sitrred for 1 hour. The methoxy methyl ester is hydrolyzed by adding a 0° C. solution of 20 ml. concentrated HCL in 25 ml. methanol and stirring at 15° C. for 3 hours. The product is isolated and purified using the same general procedure in Example 1. The product, 3-carbamoyloxymethyl-7-methoxy-7β-phenylacetamido-3-cephem-4-carboxylic acid, is obtained having a m.p. of 159°–161° C., and having UV and NMR spectra consistent with the assigned structure.

EXAMPLE 3

3-Carbamoyloxymethyl-7-methoxy-7β-(2-furylacetamido)-3-cephem-4-carboxylic Acid

The dimethoxymethyl ester of 7β-(D-5-tosylamino-5-carboxyvaleramido)-3-carbamoyloxymethyl-7-methoxy-3-cephem-4-carboxylic acid is reacted with 2-furylacetyl chloride in the presence of 12 gm. of hydrated type 4A molecular sieves (hydrated to 15% ± 2% water), following the procedures just described. The side chain, and ester blocking group are removed also following the procedures described. The product obtained is 3-carbamoyloxymethyl-7-methoxy-7β-(2-furylacetamido)-3-cephem-4-carboxylic acid, m.p. 156°–161° C., UV (pH 7.0 buffer)λmax. 265 nm ε7200 and having IR and NMR consistent with the structure.

In the same manner, the product 3-carbamoyloxymethyl-7-methoxy-7β-thiophenoxyacetamido-3-cephem-4-carboxylic acid is prepared, using phenylthioacetyl chloride instead of 2-furyl acetyl chloride. The product has a m.p. of 119°–123° C., UV (pH 7.0 buffer)λ max. 247 nm ε10400 and a consistent NMR spectrum.

EXAMPLE 4

Sodium 7-(2-thienylacetamido)-7-methoxy-3-carbamoyloxymethyl-3-cephem-4-carboxylate Step A:
7β-(D-5-benzoylamino-5-carboxyvaleramido)-3-carbamoyloxymethyl-7-methoxy-3-cephem-4-carboxylic Acid, disodium salt To 500 ml. of an aqueous solution containing 48.5 mM of mono-sodium 7β-(D-5-amino-5-carboxyvaleramido)-3-carbamoyloxymethyl-7-methoxy-3-cephem-4-carboxylate is added enough 50% sodium hydroxide to bring the pH to 9.5. To this solution is added 15 ml. [128 mM] of benzoyl chloride with vigorous stirring. The pH is maintained at 9.5 over 30 minutes by the addition of caustic soda upon demand.

The pH of the solution is then adjusted to 4.0 with concentrated hydrochloric acid, and washed twice with ethyl acetate.

The aqueous cut is cooled to 0° C., and 200 ml. of isopropanol, and 300 ml. of ethyl acetate added while stirring. The pH is adjusted to 2.0 with hydrochloric acid. The organic cut is separated and the aqueous reextracted three times with ethyl acetate. The combined extracts are washed with sodium chloride solution, dried with sodium sulfate and concentrated in vacuo to yield 43.0 grams of a dark oil.

The oil is dissolved in 200 ml. of ethanol and a solution of 30 g. of 2-ethyl hexanoic acid sodium salt added. The slurry is cooled to 0° C., filtered, washed with ethanol and dried in vacuo to yield 28.8 g. [102%] of disodium 7β-(D-5-benzoylamino-5-carboxyvaleramido)-3-carbamoyloxymethyl-7-methoxy-3cephem-4-carboxylate which was 67% pure by chromatographic comparison with a pure standard.

Step B: Dimethoxymethyl ester of 7β-(D-5-benzoylamino-5-carboxyvaleramido)-3-carbamoyloxymethyl-7-methoxy-3cephem-4-carboxylic Acid To a slurry of 20 g. of disodium 7β-(D-5-benzoylamino-5-carboxyvaleramido)-3-carbamoyloxymethyl-7-methoxy-3-cephem-4-carboxylate in 200 ml. of acetonitrile at 0° C. is added dropwise 16 ml. of 6M chloromethylmethyl ether over 90 min. After 1 hour addition time 6 ml. of S-collidine is added. The slurry is stirred for an additional 2 hours at 0° C. The mixture is then diluted with 500 ml. of methylene chloride and washed twice with dilute phosphoric acid once with dilute sodium bicarbonate and once with 5% sodium chloride. The aqueous cuts are back washed with 50 ml. of methylene chloride. The organic phase is dried with sodium sulfate and concentrated in vacuo to about 100 ml.

The solution is passed through 200 ml. of Silica Gel G, washed with 200 ml. of methylene chloride, then eluted with 800 ml. of ethyl acetate. The ethyl acetate eluates are concentrated in vacuo to yield 18.5 grams of yellow oil.

The crude is recrystallized from 50 ml. of ethyl acetate to yield 10.0 g. [67%] of dimethoxymethyl ester of 7β-(D-5-benzoylamino-5-carboxyvaleramido)-3-carbamoyloxymethyl-7-methoxy-3-cephem-4-carboxylic acid.

Step C: Sodium 7-(2-thienylacetamido)-7-methoxy-3-carbamoyloxymethyl-3-cephem-4-carboxylate A slurry containing 192 mg. (0.3 mM) of dimethoxymethyl ester of 7β-(D-5-benzoylamino-5-carboxyvaleramido)-3-carbamoyloxymethyl-7-methoxy-3-cephem-4-carboxylic acid, 225 mg. pulverized Linde-type 4A molecular sieves containing 10% ± 2% water, 0.3 ml. of 2-thienylacetyl chloride and 4 ml. of dichloroethane is refluxed with vigorous stirring for 4hours. The mixture is cooled to 65° C., and 10 ml. of 0.05M t-butanol in dichloroethane added over 2 hours, then heated an additional 1 hr. at 65° C. The reaction mixture is cooled to 0° C., filtered and washed with 5 ml. of methanol. The filtrate is cooled to 0° C. with stirring, then 1.4 ml. of 1:1 hydrochloric acid:methanol is added, and the resultant mixture stirred at about 15° C. for 3 hours. The mixture is poured into 10 ml. of water containing 1.6 g. of sodium bicarbonate. The organic phase cuts are discarded. The aqueous cuts are assayed for a 65% yield of the product, sodium 7-(2-thienylacetamido)-7-methoxy-3-carbamoyloxymethyl-3-cephem-4-carboxylate.

Step D:

In analogous fashion, p-chlorobenzoyl chloride, p-nitrobenzyl chloride, or toluoyl chloride are employed in Step A. The ultimate yield of the desired product sodium 7-(2-thienylacetamido)-7-methoxy-3-carbamoyloxymethyl-3-cephem-4-carboxylate in each case, is, respectively: 70%; 68%; and 72%.

EXAMPLE 5

Sodium 7-(2-thienylacetamido)-7-methoxy-3-carbamoyloxymethyl-3-cephem-4-carboxylate A mixture of 2.76 g. (4 mmoles) of the dimethoxymethyl ester of 7β-(D-5-tosylamino-5-carboxyvaleramido)-3-carbamoyloxymethyl-7α-methoxy-3-cephem-4-carboxylate, 3 g. of dry Linde-type 4A molecular sieves, having less than 2% water, 2 ml. of thienylacetyl chloride (16 mmoles) in 34 ml. of dichloroethane is stirred at reflux for 5 hours t-Butanol, 0.38 ml. (4 mmoles) is then added and stirring continued for 2 hours. At the end of this period, another 0.095 ml. (1 mmole) of t-butanol is introduced and the reaction mixture was stirred at reflux for another ½ hr. The reaction mixture is cooled to 0°-5° C. in an ice-water bath. The molecular sieves are removed by suction-filtration and then washed with 40 ml. of ice-cold methanol. The filtrate and wash were combined and cooled to 0° C. An ice-cold solution of 8.3 ml. concentrated HCl and 9.5 ml. MeOH is added and the solution warmed to 15° C. and stirred at 15° C. for 2 hrs. 40 min. When the hydrolysis is complete the reaction is quenched by adding to a suspension of 22 g. sodium bicarbonate in 120 ml. of water at 0°-5° C. The two-phase solution is stirred for 10 min. The heavy salt deposit that forms is removed by filtration and washed with a small amount of 5% NaCl solution containing 0.5% sodium bicarbonate. The dichloroethane layer is separated and extracted with 2 × 20 ml. of a solution of 0.5% NaHCO₃ + 5% NaCl. The aqueous fractions are combined and washed with 20 ml. of dichloroethane. The bicarbonate solution was assayed by liquid chromatography to contain 73% sodium 7-(2-thienylacetamido)-7-methoxy-3-carbamoyloxymethyl-3-cephem-4-carboxylate and 2.1% of the unchanged starting material.

EXAMPLES 6–19

Sodium 7-(2-thienylacetamido)-7α-methoxy-3-carbamoyloxymethyl-3-cephem-4-carboxylate Following the general procuedure outlined in Example 6, 4 mmoles (2.8 g.) of the dimethoxymethyl ester of 7β-(D-5-tosylamino-5-carboxyvaleramido)-3-carbamoyloxymethyl-7α-methoxy-3-cephem-4-carboxylate is reacted using the following tabulated amounts of reagents and reaction conditions. The entire reaction time in each case is about 16 hours. The molecular sieves employed, in each case, are Linde-type 4A which are heated to 700° C. before the reaction, exhibiting a weight loss of about 3% on drying. The sieves are calculated to be substantially anhydrous, having less than 2% water content, by weight. The temperature of the reaction in each case is 67° C.

| Example | 4A Sieves Amount g. | Thienylacetyl Chloride Mmole | Index Cleavage Agents | Amount Mmole | Time[a] Hrs. | Final Product Yield % | Starting Material Yield % |
|---|---|---|---|---|---|---|---|
| 6 | 3 | 16 | HCl | 0.4<br>0.8<br>0.8 | 3<br>1 | 69 | 4.5 |
| 7 | 3 | 16 | Isopropanol | 3<br>1<br>1 | 3<br>1<br>1 | 68 | 6.2 |
| 8 | 3 | 16<br>4[b] | Isopropanol<br>Isopropanol | 2.4<br>2<br>2 | 3<br>1<br>1 | 67 | 3.1 |
| 9 | 3 | 16 | Isopropanol | 5<br>1 | 3<br>2 | 62 | 10.7 |
| 10 | 3 | 16 | Isopropanol | 5<br>5 | 2<br>2 | 48 | 6.2 |
| 11 | 3 | 16 | t-Butanol | 5<br>5 | 3<br>2 | 70 | 5.8 |
| 12 | 1.5[c] | 16 | t-Butanol | 5<br>5 | 2<br>1 | 69.5 | 3.6 |
| 13 | 0[d] | 16 | — | — | — | 5.2 | 0.4 |
| 14 | 3 | 16 | t-Butanol | 10 | 1.5 | 64 | 4.1 |
| 15 | 3 | 16 | t-Butanol | 10 | 1.5 | 58 | 0.5 |
| 16 | 3 | 16 | t-Butanol | 10 | 1.5 | 28 | 1.1 |
| 17 | 3 | 16 | t-Butanol | 5 | 1.5 | 64.5 | 5.2 |
| 18 | 2[e] | 12 | t-Butanol | 5<br>5<br>5 | 2<br>5 | 67 | 8.2 |
| 19 | 2[e] | 24 | t-Butanol | 5<br>5 | 2<br>1 | 68.5 | 3.1 |

[a]Time between portionwise addition of imide cleavage agents.
[b]Addition after 3 hours cleavage with isopropanol and reaction was continued for another 16 hours before the final imide cleavage.
[c]Another amount of 1.5 g. sieves was added at the end of the transacylation period and before the addition of alcohol.
[d]Transacylation period was 1 ½ hours.
[e]Another amount of 1 g. sieves was added at the end of the transacylation.

EXAMPLES 20–24

The same general procedure used in Examples 6–19 is employed, except that the reaction temperature is changed as indicated in the tabulated data. The reaction mixture is 4 mmoles (2.8 g.) of the dimethoxymethyl ester of 7β-(D-5-tosylamino-5-carboxyvaleramido)-3-carbamoyloxymethyl-7α-methoxy-3-cephem-4-carboxylate, 3 g. dried Linde-type 4A sieves (less than 2% water by weight) and 16 mmoles thienylacetyl chloride in 34 ml. of dichloroethane.

| Example | Transacylation Period Hours | Temp. C. | Imide Cleavage Agents | Amount Mmole | Time Hours | Final Product Yield % | Starting Material Yield % |
|---|---|---|---|---|---|---|---|
| 20 | 25 | 55 | Isopropanol | 5<br>5 | 8.5<br>3.0 | 25 | 7.2 |

-continued

| Example | Transacylation Period Hours | Temp. C. | Imide Cleavage Agents | Amount Mmole | Time Hours | Final Product Yield % | Starting Material Yield % |
|---|---|---|---|---|---|---|---|
| 21 | 16 | 67 | Isopropanol | 5 5 | 3 2 | 70 | 5.8 |
| 22 | 7 | 78 | Isopropanol | 4 | 2 | 71.5 | 5.2 |
| 23 | 5 | 86 | Isopropanol | 4 | 1.5 | 67 | 4.1 |
| 24 | 5 | 86 | Isopropanol | 4 1 | 2 0.5 | 73 | 2.1 |

The final product in all cases is sodium 7-(2-thienylacetamido)-7α-methoxy-3-carbamoyloxymethyl-3-cephem-4-carboxylate.

EXAMPLE 25
7-(2-Thienylacetamido)-7-methoxy-3-carbamoyloxymethyl-3-cephem-4-carboxylic Acid One gram of sodium 7β-(D-5-amino-5-carboxyvaleramido)-3-carbamoyloxymethyl-7-methoxy-3-cephem,-4-carboxylate to a reaction vessel containing 20 ml. of dichloroethane. To this is added 1 g. of Linde molecular sieves type 4A powder having 15% water and 8 mmoles (1 ml.) thienylacetyl chloride. The slurry is heated at reflux for 8 hours. After filtering the molecular sieves are washed with methanol. The methanol wash of the sieves is analyzed and contains a 25% yield of the desired product, 7β-(2-thienylacetamido-7α-methoxy-3-carbamoyloxymethyl-3-cephem-4-carboxylic acid, by tlc and liquid chromatography assay. The dichloroethane layer of the reaction mixture is extracted with 5% NaHCO3 and shown by tlc and liquid chromatography to contain another 5% of the desired product. Thin layer chromatography of the organic layer at this point shows the presence of the mixed anhydride; after removal of the solvent by evaporation, the mixed anhydride is hydrolyzed in 50% acetone-water (50 ml.) in the presence of 10 mole % pyridine. Tlc and liquid chromatography shows the production of another 13% of the final product free acid. The total yield is 156 mg. of the acid, 23% yield.

What is claimed is:

1. The process of preparing a compound of the formula:

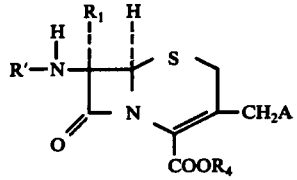

wherein
$R_1$ is hydrogen or methoxy;
A is carbamoyloxy or loweralkanoyloxy;
R' is an acyl group having the formula:

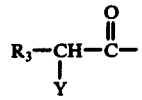

wherein
Y is hydrogen, carboxy, —$NHR_2$ or —$OR_5$;
$R_2$ is hydrogen, trichloroethoyxcarbonyl, tertiary butoxycarbonyl, benzoylmethoxycarbonyl, trimethylsilyl, p-methoxybenzyloxy, 2-nitrophenylsulfenyl, 2,4,-dinitrophenylsulfenyl, chloroacetyl, p-nitrophenylthio, p-nitrobenzenesulfonyl, p-toluenesulfonyl, methanesulfonyl, benzoyl, p-chlorobenzoyl, p-nitrobenzoyl or toluoyl;
$R_3$ is phenyl, 2-thienyl, 3-thienyl, 2-furyl, 3-furyl, 1-tetrazoyl, $C_1$-$C_4$ loweralkylphenyl, halophenyl, hydroxyphenyl, a $C_1$-$C_4$ loweralkyloxyphenyl;
$R_4$ is methyl, ethyl, tertiary butyl, phthalimidomethyl, succinimidomethyl, phenacyl, p-bromophenacyl, 2,2,2-trichloroethyl, 2-methylthioethyl, 2-(p-methylphenyl)ethyl, 2-(p-methylphenyl)sulfonylethyl, 2-methylaminoethyl, 2-chloro-(or bromo)ethyl, benzyl, p-nitrobenzyl, p-methoxybenzyl, 3,5-dinitrobenzyl, 2,4,6-trimethylbenzyl, 3,5-dichloro-4-hydroxybenzyl, benzhydryl, p-methoxybenzhydryl, acetoxymethyl, pivaloyloxymethyl, methoxymethyl, p-nitrophenyl or 3,5-dinitrophenyl, acetyl, benzoyl or thienylacetyl;
$R_5$ is hydrogen, methyl, ethyl, phenacyl, p-bromophenacyl, 2,2,2-trichloroethyl, benzyl, p-nitrobenzyl, p-methoxybenzyl, 3,5-dinitrobenzyl, 2,4,6-trimethylbenzyl, benzhydryl, p-methoxybenzhydryl or methoxymethyl; which consisting essentially of reacting a compound of the formula:

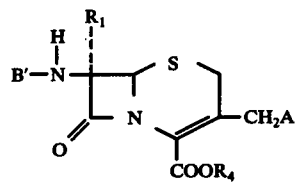

wherein
B' is

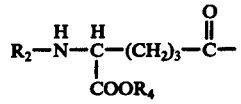

wherein
$R_2$, $R_4$ are as defined above; or an acyl group R' which is different than the final desired substituent; with an acylating agent having the formula:

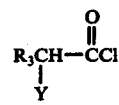

wherein
$R_3$ and Y are the same as before defined, in the presence of a synthetic zeolite of the type 3A, 4A, 5A, or 13X, containing from about 0 to 30% by weight water of hydration; and then cleaving B' by either prolonging the reaction time to between about 30 minutes to about 30 hours; or by adding a loweralkanol of 1 to 6 carbon atoms, loweralkylthiol of 1 to 6 carbon atoms, benzyl alcohol or hydrochloric acid to yield the final product, and recovering the final product.

2. The process of claim 1 wherein the synthetic zeolite is employed in approximately 0.5 to 2 times the amount by weight of the starting material.

3. The process of claim 2 wherein the synthetic zeolite is employed in approximately equal, or slightly greater amounts (weight basis) of the starting material.

4. The process of claim 1 wherein the interchange reaction takes place in a solvent inert to the reactants.

5. The process of claim 1 wherein $R_1$ is methoxy.

6. The process of claim 5 wherein R' is 2-thienylacetyl.

7. The process of claim 5 wherein R' is 1-tetrazolylacetyl.

8. The process of claim 5 wherein R' is 2-(—$NHR_2$)-2-phenylacetyl, wherein $R_2$ is hydrogen or trichloroethoxycarbonyl, tertiary butoxycarbonyl, benzoylmethoxycarbonyl, trimethylsilyl, p-methoxybenzyloxy, 2-nitrophenylsulfenyl, 2,4-dinitrophenylsulfenyl, chloroacetyl, p-nitrophenylthio, p-nitrobenzenesulfonyl, p-toluenesulfonyl, methanesulfonyl, benzoyl or toluoyl.

9. The process of claim 5 wherein R' is 2-($OR_5$)-2-phenylacetyl, wherein $R_5$ is hydrogen, methyl, ethyl, phenacyl, p-bromophenacyl, 2,2,2-trichloroethyl, benzyl, p-nitrobenzyl, p-methoxybenzyl, 3,5-dinitrobenzyl, 2,4,6-trimethylbenzyl, benzhydryl, p-methoxybenzhydryl or methoxymethyl.

10. The process of claim 1 wherein A is carbamoyloxy.

11. The process of claim 1 wherein $R_4$ is methoxymethyl, benzyl, benzhydryl, methylthiomethyl, methylthioethyl, or 2-butenyl.

12. The process of claim 11 wherein $R_4$ is methoxymethyl.

13. The process of claim 1 wherein A is loweralkanoyloxy of 1–6 carbon atoms.

14. The process of claim 13 wherein A is acetoxy.

15. The process of claim 14 wherein $R_4$ is methoxymethyl.

16. The process of preparing the compound:

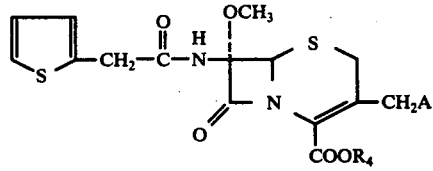

wherein
$R_4$ is hydrogen, or methyl, ethyl, tertiary butyl, phthalimidomethyl, succinimidomethyl, phenacyl, p-bromophenacyl, 2,2,2-trichloroethyl, 2-methoxythioethyl, 2-(p-mthylphenyl)-ethyl, 2-(p-methylphenyl)sulfonylethyl, 2-methylaminoethyl, 2-chloro(or bromo)ethyl, benzyl, p-nitrobenzyl, p-methoxybenzyl, 3,5-dinitrobenzyl, 2,4,6-trimethylbenzyl, 3,5-dichloro-4-hydroxybenzyl, benzhydryl, p-methoxybenzhydryl, acetoxymethyl, pivaloyloxymethyl, methoxymethyl p-nitrophenyl, 3,5-dinitrophenyl, acetyl, benzoyl or thienylacetyl; and A is carbamoyloxy or acetoxy;

which consists essentially of reacting the starting compound of the formula:

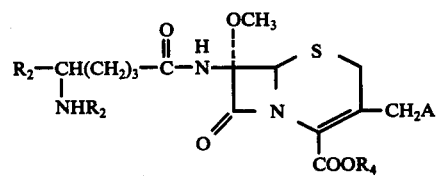

wherein
A is carbamoyloxy or acetoxy; and $R_2$ is hydrogen, or trichloroethoxycarbonyl, tertiary butoxycarbonyl, benzoylmethoxycarbonyl, trimethylsilyl, p-mthoxybenzyloxy, 2-nitrophenylsulfenyl, 2,4-dinitrophenylsulfenyl, chloroacetyl, p-nitrophenylthio, p-nitrobenzenesulfonyl, p-toluenesulfonyl, methanesulfonyl, benzoyl, p-chlorobenzyl, p-nitrobenzoyl, or toluoyl;

with 2 to 4 molar excess of 2-(2-thienyl)-acetyl chloride; from about 0.5 to about 2 times (weight basis) of a synthetic zeolite, type 3A, 4A, 5A, or 13X, containing from about 0 to 30% by weight water of hydration;

at a temperature of between about 50°–90° C;

in an inert solvent;

for a period of from about 30 minutes to 30 hours;

then optionally adding from about 0.5 molar equivalent to about 3 molar equivalents, based on the amount of the starting compound, of a cleaving agent which is (1) lower alcohol of 1–6 carbon atoms, (2) loweralkyl thiol of 1–6 carbon atoms, (3) benzyl alcohol, or (4) hydrochloric acid, and recovering the desired product.

17. The process of claim 16 wherein the lower alcohol is isopropanol or t-butanol.

18. The process of claim 16 wherein the cleaving agent is hydrochloric acid.

* * * * *